United States Patent [19]
Hamayasu et al.

[11] Patent Number: 5,763,598
[45] Date of Patent: Jun. 9, 1998

[54] BRANCHED CYCLODEXTRINS AND METHOD FOR PRODUCING THEM

[75] Inventors: Kenichi Hamayasu; Tetsuya Ito; Koki Fujita; Kozo Hara, all of Yokohama; Kyoko Koizumi, Fujiidera; Toshiko Tanimoto, Nishinomiya; Hirofumi Nakano, Toyonaka; Sumio Kitahata, Sennan-gun, all of Japan

[73] Assignee: Ensuiko Sugar Refining Co., Ltd., Yokohama, Japan

[21] Appl. No.: 876,979

[22] Filed: Jun. 16, 1997

[30] Foreign Application Priority Data

Jul. 11, 1996 [JP] Japan .................................. 8-199534

[51] Int. Cl.$^6$ .................. C08B 37/16; A61K 31/715; A01N 43/04
[52] U.S. Cl. ..................... 536/46; 536/103; 514/58
[58] Field of Search ............... 536/46, 103; 514/58

[56] References Cited

FOREIGN PATENT DOCUMENTS 08173181  7/1996  Japan .
8-325304  10/1996  Japan .

*Primary Examiner*—John Kight
*Assistant Examiner*—Everett White
*Attorney, Agent, or Firm*—Frishauf, Holtz, Goodman, Langer & Chick, P.C.

[57] ABSTRACT

Disclosed are novel branched cyclodextrins having any of an N-acetylglucosamine group, a glucosaminyl group, an N-acetylgalactosaminyl group and a galactosaminyl group as bonded to the hydroxyl group of the cyclodextrin ring by β-bonding therebetween, and their salts. The novel branched cyclodextrins are produced by reacting a solution containing a cyclodextrin and an N-acetylglucosamine or N-acetylgalactosamine with an N-acetylhexosaminidase, and optionally deacetylating the resulting product.

16 Claims, 8 Drawing Sheets

C : Signal derived from the carbon of glucoses constituting CD ring
C': Signal derived from the carbon of glucoses bonded to GlcNAc
N : Signal derived from the carbon of the side chain GlcNAc

C: Signal derived from the carbon of glucoses constituting CD ring
C': Signal derived from the carbon of glucoses bonded to GlcNAc
N: Signal derived from the carbon of the side chain GlcNAc

C: Signal derived from the carbon of glucoses constituting CD ring
C': Signal derived from the carbon of glucoses bonded to GalNAc
N: Signal derived from the carbon of the side chain GalNAc

BRANCHED CYCLODEXTRINS AND METHOD FOR PRODUCING THEM

FIELD OF THE INVENTION

The present invention relates to branched cyclodextrins and a method for producing them. Particularly, it relates to N-acetylglucosaminyl-cyclodextrins where the N-acetylglucosaminyl group is bonded to the hydroxyl group of the cyclodextrin (hereinafter referred to as CD) ring by β-bonding therebetween; glucosaminyl-CDs where the glucosaminyl group is bonded to the hydroxyl group of the CD ring by β-bonding therebetween, and their salts; N-acetylgalactosaminyl-CDs where the N-acetylgalactosaminyl group is bonded to the hydroxyl group of the CD ring by β-bonding therebetween; galactosaminyl-CDs where the galactosaminyl group is bonded to the hydroxyl group of the CD ring by β-bonding therebetween, and their salts; and also relates to a method for producing these branched CDs through enzymatic reaction.

BACKGROUND OF THE INVENTION

CD is a cyclic dextrin comprising glucoses as bonded to each other by α-1,4 bonding therebetween; and well known are α-, β- and γ-CDs each comprising 6, 7 and 8 glucoses, respectively. Recently have been produced branched CDs with improved solubility, in which a substituent, such as a glucosyl or maltosyl group, is bonded to the CD ring by α-1,6 bonding.

As having therein intramolecular cavities which are hydrophobic, these CDs and branched CDs are capable of forming inclusion complexes and therefore have the property of taking various oily substances in themselves. As having the property, such CDs and branched CDs are widely used in the field of food industry, cosmetic industry and medical industry.

In particular, in the field of medical industry, it is specifically noticed that poorly soluble drugs are complexed with branched CDs to thereby increase their solubility, resulting in the increase in the bioavailability of the drugs.

In order to reduce harmful side effects of drugs, various studies are being made on the properties of saccharides with specific cell recognition to utilize them as the sensors for drug carriers to the targeted cells in drug delivery systems. In particular, it is well known that galactose has a strong affinity for liver tissues and that mannose has a strong affinity for liver parenchyma cells, liver non-parenchyma cells and macrophages.

Utilizing transglycosylation and condensation reaction of enzyme, we have already succeeded in the production of galactosyl-CDs and mannosyl-CDs having a galactosyl or mannosyl group as bonded to the glucosyl group of the CD ring. In addition, we also have already succeeded in the production of galactosyl-branched CDs and mannosyl-branched CDs having a galactosyl or mannosyl group as bonded to the glucosyl group in the side chain of the branched CD ring.

On the other hand, N-acetylglucosamine and its deacetylated derivative, glucosamine are saccharides constituting chitin that is the essential component existing in shells of crabs, lobsters, etc. These are the basic saccharide moieties that constitute the glycochains of various saccharides which play an important role in cell recognition.

Similarly, one analog of N-acetylglucosamine, N-acetylgalactosamine is also the basic saccharide moiety constituting the glycochains of various saccharides which play an important role in cell recognition.

Utilizing the forming inclusion complexes of CDs and the above-mentioned properties of N-acetylglucosamine and glucosamine, we, the present inventors have made various attempts at producing N-acetylglucosaminyl-CDs having an N-acetylglucosaminyl group as bonded to the CD ring, in order to apply them to drug delivery systems and also to apply them to the solubilization of poorly soluble drugs.

We have previously found out that lysozyme and other N-acetylglucosaminidases are effectively used in producing N-acetylglucosaminyl-branched CDs having an N-acetylglucosaminyl group as bonded to the hydroxyl-group in the branched side chain of the branched CD ring by transferred β-bonding, from N-acetyl-chitooligosaccharides (see Japanese Patent Kokai No. 8-325304 (325304/1996)).

However, the above-mentioned method is problematic in that the N-acetyl-chitooligosaccharides to be used as the saccharide donors are expensive.

In addition, although lysozyme and other N-acetylglucosaminidase used therein can act on the acceptor, branched CD to thereby make the N-acetylglucosaminyl group bonded to the branched side chain moiety thereof, they could not act to bond such an N-acetylglucosaminyl group directly to α-, β- and γ-CDs having no branched chain.

SUMMARY OF THE INVENTION

Given the situation, we, the present inventors have further studied and now have found that N-acetylhexosaminidases are effective in efficiently producing an N-acetylglucosaminyl-CD or N-acetylgalactosaminyl-CD from a mixture of an N-acetylglucosamine or N-acetylgalactosamine and a CD. On the basis of this finding, we have completed the present invention.

Accordingly, the present invention relates to branched CDs having any of N-acetylglucosaminyl, glucosaminyl, N-acetylgalactosaminyl and galactosaminyl groups as bonded to the hydroxyl group of the CD ring by β-bonding, and their salts. It also relates to a method for producing the above-mentioned branched CDs, which comprises reacting an N-acetylhexosaminidase with a solution containing a CD and an N-acetylglucosamine or N-acetylgalactosamine, and optionally deacetylating the resulting product.

DETAILED DESCRIPTION OF THE INVENTION

Now, the present invention is described in detail hereinunder.

The branched CDs of the present invention are all novel substances, specific examples of which include, for example, 6-O-β-D-N-acetylglucosaminyl-α-CD, 6-O-β-D-N-acetylglucosaminyl-β-CD, 6-O-β-D-N-acetylglucosaminyl-γ-CD, 6-O-β-D-N-acetylgalactosaminyl- α-CD, 6O-β-D-N-acetylgalactosaminyl-β-CD, 6O-β-D-N-acetylgalactosaminyl-γ-CD, 6-O-β-D-glucosaminyl-α-CD, 6-O-β-D-glucosaminyl-β-CD, 6-O-β-D-glucosaminyl-γ-CD, 6-O-β-D-galactosaminyl-α-CD, 6-O-β-D-galactosaminyl-β-CD, 6-O-β-D-galactosaminyl-γ-CD, 3-O-β-D-N-acetylglucosaminyl-α-CD, 3-O-β -D-N-acetylglucosaminyl-β-CD, 3-O-β-D-N-acetylglucosaminyl-γ-CD, 3-O-β-D-N-acetylgalactosaminyl-α-CD, 3-O-β-D-N-acetylgalactosaminyl-β-CD, 3-O-β-D-N-acetylgalactosaminyl-γ-CD, 3-O-β-D-glucosaminyl-α-CD, 3-O-β-D-glucosaminyl-β-CD, 3-O-β-D-glucosaminyl-γ-CD, 3-O-β-D-galactosaminyl-α-CD, 3-O-β-D-galactosaminyl-β-CD, 3-O-β-D-galactosaminyl-γ-CD, 2-O-β-D-N-acetylglucosaminyl-α-CD, 2-O-β-D-N-acetylglucosaminyl-β-CD, 2-O-β-D-N-acetylglucosaminyl-γ-CD, 2-O-β-D-N-acetylgalactosaminyl-α-CD, 2-O-β-D-N-acetylgalactosaminyl-β-CD, 2-O-β-D-N-acetylgalactosaminyl-γ-CD, 2-O-β-D-glucosaminyl-α-CD, 2-O-β-D-glucosaminyl-β-CD, 2-O-glucosaminyl-γ-CD, 2-O-β-D-galactosaminyl-α-CD, 2-O-βD-galactosaminyl-β-CD, 2-O-β-D-galactosaminyl-γ-CD, etc.

Of these, the structural formulae (Nos. 1 to 12) of typical compounds are shown below, in which n means from 5 to 7.

Structural Formula 1:

Structural Formula 2:

Structural Formula 3:

Structural Formula 4:

-continued

Structural Formula 5:

Structural Formula 6:

Structural Formula 7:

Structural Formula 8:

Structural Formula 9:

Structural Formula 10:

Structural Formula 11:

Structural Formula 12:

The branched CDs of the present invention can be produced by reacting an N-acetylhexosaminidase with a solution containing a CD and an N-acetylglucosamine or N-acetylgalactosamine, and thereafter optionally deacetylating the resulting product.

The deacetylation may be conducted by any known method, for example, including a method of reacting the product with an alkaline solution (see Sannan, T., Kurita, K., Iwakura, Y.; Makromol. Chem., 177, 3589–3600, 1976), and a method of processing the product with an ion-exchange resin.

Any of α-CD, β-CD and γ-CD is essentially used as the starting CD in the present invention. However, also employable herein is any CD having a branched chain of a substituent, such as glucosyl-CD, maltosyl-CD, mannosyl-CD or galactosyl-CD, as bonded to the hydroxyl group of the CD ring by α-1,6 bonding. A mixture of these is also employable.

It is desirable that the N-acetylglucosamine and N-acetylgalactosamine to be used in the present invention are of high purity. However, those containing oligosaccharides are also employable.

Any and every enzyme can be used in the present invention, including, for example, N-acetylhexosaminidases, N-acetylglucosaminidases and N-acetylgalactosaminidases, provided that the enzyme may act on the solution containing an N-acetylglucosamine or N-acetylgalactosamine and a CD, while enzymatically catalyzing the condensation between the two, or that is, the reaction therebetween opposite to hydrolysis, thereby bonding the N-acetylglucosaminyl or N-acetylgalactosaminyl group to CD by β-bonding therebetween to give the intended N-acetylglucosaminyl-CD or N-acetylgalactosaminyl-CD.

Such enzymes for use in the present invention exist widely in the natural field. For example, known are plant derived N-acetylhexaminidase that may be extracted from jack bean (*Canavalia ensiformis*); animal derived N-acetylglucosaminidase that may be extracted from bovine kidneys; and microorganism derived N-acetylglucosaminidase that may be produced by *Aspergillus niger*. Also known is animal derived N-acetylgalactosaminidase that may be extracted from trumpet shells; and microorganism derived N-acetylgalactosaminidase that may be extracted from microbes of Acremonium.

In the reaction system of the present invention, it is desirable that the CD concentration in the solution (aqueous solution or suspension) containing a CD and an N-acetylglucosamine or N-acetylgalactosamine is from about 1 to about 40% (w/w) while the N-acetylglucosamine or N-acetylgalactosamine concentration therein is from about 5 to about 50% (w/w). In this, it is suitable that the ratio by weight of N-acetylglucosamine or N-acetylgalactosamine to CD falls within the range between 1/10 to 50/1, but preferably within the range between 1/1 to 5/1.

The pH of the reaction system may fall between 3 and 10, preferably between 4 and 7; and the reaction temperature may fall between 20° C. and 70° C., preferably between 40° C. and 60° C.

As having close relation to the reaction time, amount of the enzyme to be used may be such that the reaction is finished within a period of time of from 5 to 200 hours, preferably from 10 to 50 hours, which, however, is not limitative.

The deacetylation may be conducted according to any ordinary method, as so mentioned hereinabove. For example, the N-acetylglucosaminyl-CD or N-acetylgalactosaminyl-CD may be treated with an alkaline solution. For the conditions for this treatment, referred to are those for ordinary methods. For example, in the reaction system for deacetylation, the concentration of the N-acetylglucosaminyl-CD or N-acetylgalactosaminyl-CD may be from 0.1 to 50% (w/v), preferably from 0.5 to 10% (w/v).

As the alkaline solution to be employed for the deacetylation, preferred is a solution of sodium hydroxide, which, however, is not limitative. Any one with which the intended deacetylation is effected is employable herein.

The reaction temperature, and the concentration and the type of the alkaline solution used closely influence each other. In general, therefore, it is suitable, though not limitative, that the concentration of the sodium hydroxide solution to be used is from 0.1 to 50% (w/v), that the temperature falls between 10° C. and 100° C. and the reaction time falls between 0.1 hours and 120 hours.

After the deacetylation, the reaction system is neutralized with an acid to be dropped thereinto, then desalted, and thereafter optionally purified to obtain the intended product.

The reaction mixture as obtained according to the above-mentioned process is subjected to column chromatography and high performance liquid chromatography to thereby fractionate and isolate the product, of which the molecular weight is measured through FAB-MS and of which the structure is analyzed through nuclear magnetic resonance (NMR). It has been confirmed that the products thus obtained are branched CDs such as typically those of the above-mentioned structural formulae 1 to 12.

EXAMPLES

Now, the present invention is described concretely by means of the following examples, which, however, are not intended to restrict the scope of the invention.

Example 1

(1) Condensation

To 5 ml of 20 mM citrate buffer (pH 5.0) containing 1.11 g of N-acetylglucosamine and 1.22 g of α-CD, added was 50 U of N-acetylhexosaminidase as derived from jack bean, and reacted at 45° C. for 72 hours.

Figure 1:
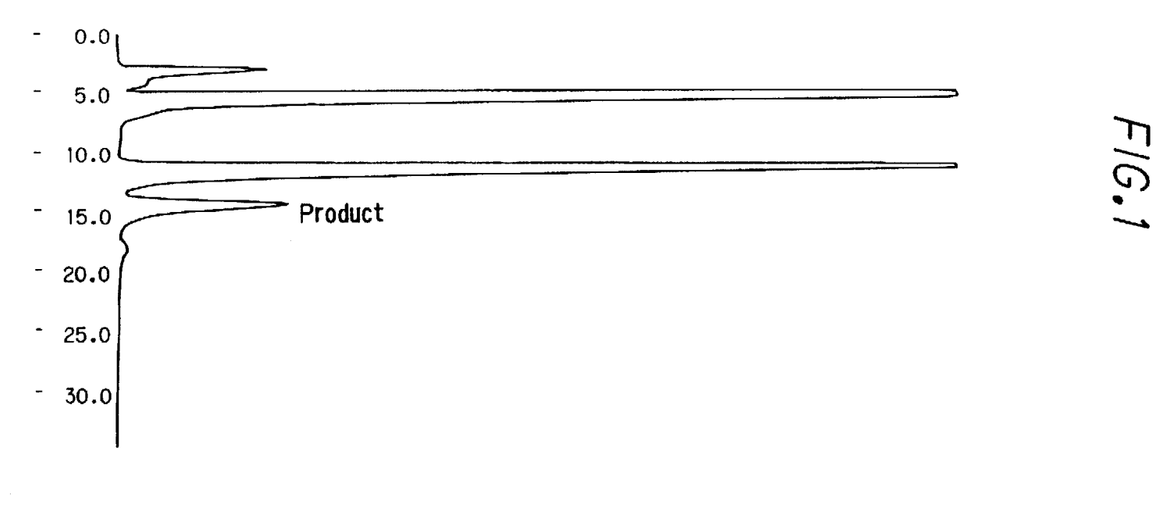
FIG. 1 is a high performance liquid chromatogram of the reaction mixture of Example 1 as passed through an amide type column.
Figure 2:
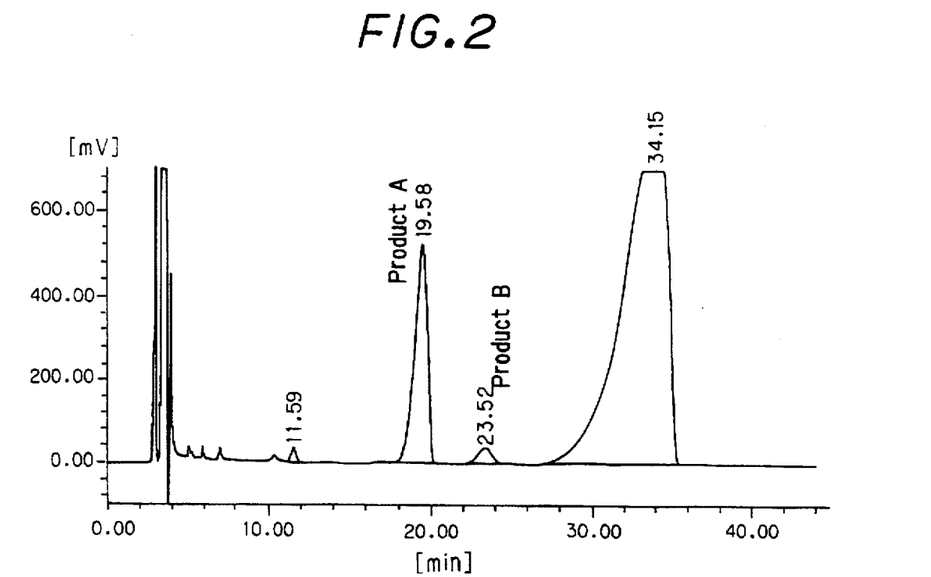
FIG. 2 is a high performance liquid chromatogram of the reaction mixture of Example 1 as passed through a reversed phase type column.

A part of the reaction mixture was analyzed through high performance liquid chromatography using an amide type column (Amide-80, produced by Toso Corp.) and that using a reversed phase column (ODS-AQ303, produced by YMC Co.). The data obtained are shown in FIG. 1 and FIG. 2.

After the reaction, the enzyme was inactivated under heat, and the resulting solution was subjected to high performance liquid chromatography using a reversed phase column, from which were fractionated 100 mg of a major product A and 5 mg of a minor product B.

(2) Structure Analysis

Figure 3:
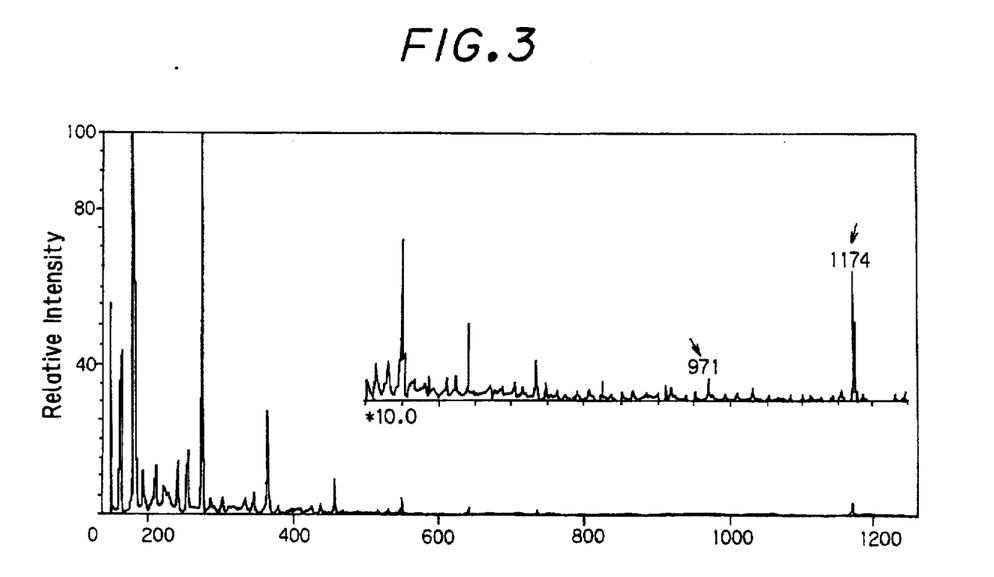
FIG. 3 is a FAB-MS spectrum of the reaction product A of Example 1.
Figure 4:
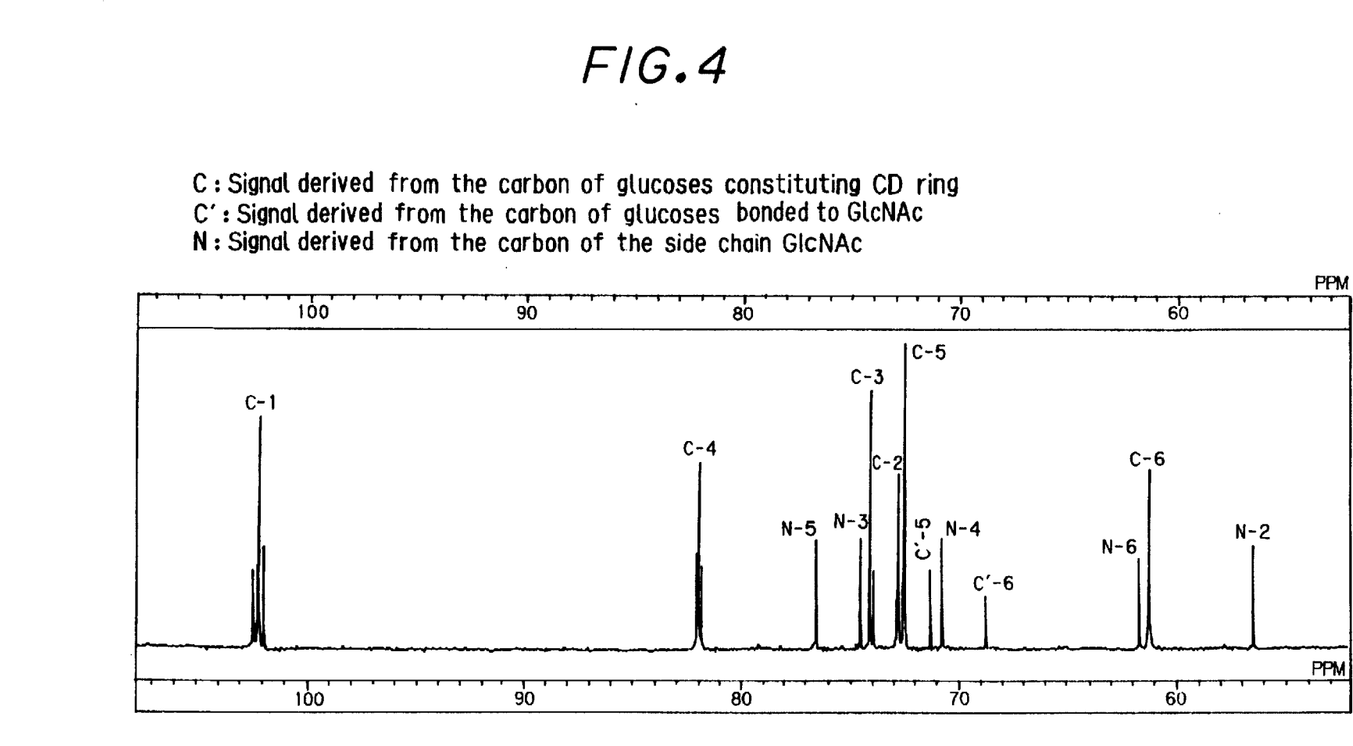
FIG. 4 is a $^{13}$C-NMR spectrum of the reaction product A of Example 1.

The major product A as isolated in the above-mentioned step (1) was found to have a molecular weight of 1175 through FAB-MS analysis, as in FIG. 3. The $^{13}$C-NMR analysis of the product A revealed that this is 6-O-β-D-N-acetylglucosaminyl-α-CD (of the above-mentioned structural formula 1, where n=5) in which the N-acetylglucosaminyl group is bonded to the 6-positioned primary hydroxyl group of the α-CD ring by β-bonding therebetween, as in FIG. 4.

On the other hand, the product B was found to have a molecular weight of 1175 through FAB-MS analysis. A small amount of the product B was dissolved in 20 mM citrate buffer (pH 5.0), then processed with N-acetylhexosaminidase, and thereafter analyzed through HPLC.

As a result, the product B was decomposed into N-acetylglucosamine and α-CD in a molar ratio of 1/1. This verifies that the product B is an iosmer (of the above-mentioned structural formula 5 or 9, where n=5) in which the N-acetylglucosaminyl group is bonded to the secondary hydroxyl group of the α-CD ring by β-bonding therebetween.

Example 2

(1) Condensation

Figure 5:
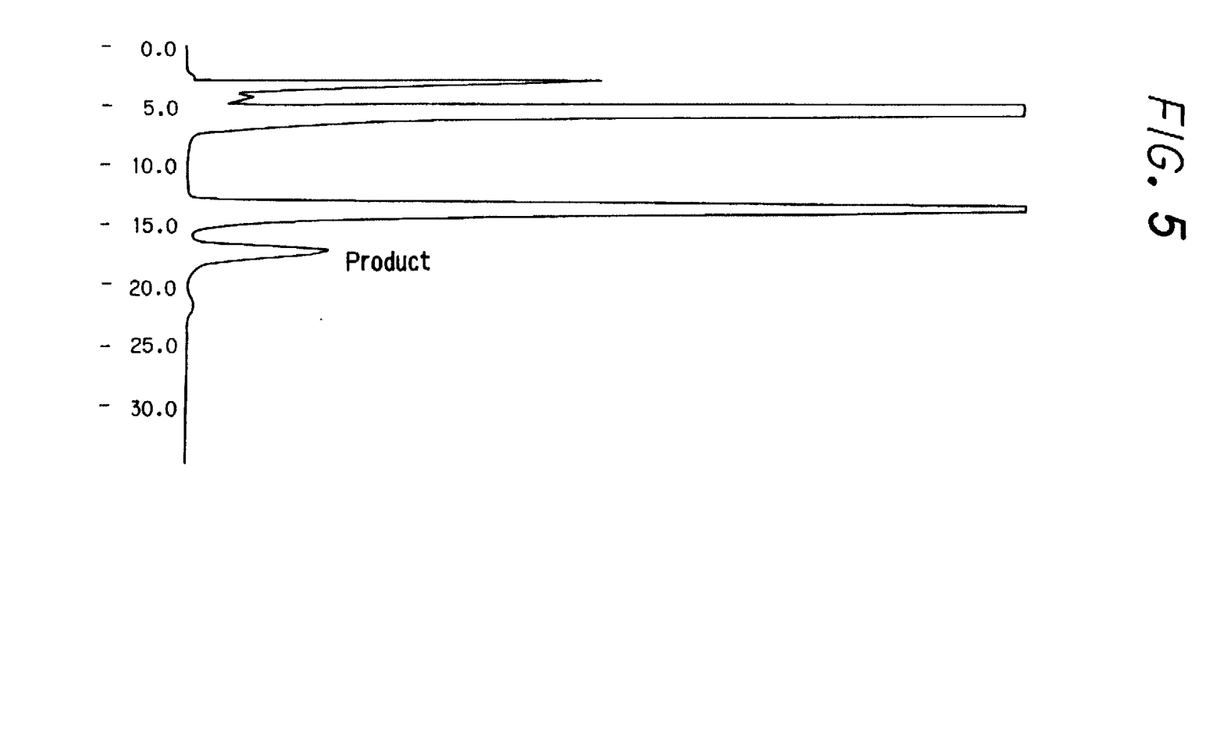
FIG. 5 is a high performance liquid chromatogram of the reaction mixture of Example 2 as passed through an amide type column.

To 5 ml of 20 mM citrate buffer (pH 5.0) containing 1.11 g of N-acetylglucosamine and 0.567 g of α-CD, added was 50 U of the same N-acetylhexosaminidase as that used in Example 1, and reacted at 45° C. for 72 hours. A part of the reaction mixture was analyzed through high performance liquid chromatography using an amide type column. The data obtained are shown in FIG. 5.

After the reaction, the enzyme was inactivated under heat, and the resulting solution was subjected to high performance liquid chromatography using a reversed phase column, from which were fractionated 40 mg of a major product C and 3 mg of a minor product D.

(2) Structure Analysis

The major product C as isolated in the above-mentioned step (1) was found to have a molecular weight of 1337 through FAB-MS analysis. Accordingly, referring to the data in Example 1, this product C was confirmed to be a compound (of the above-mentioned structural formula 1, where n=6) in which the N-acetylglucosaminyl group is bonded to the 6-positioned primary hydroxyl group of the β-CD ring by β-bonding therebetween.

On the other hand, the product D was found to have a molecular weight of 1337 through FAB-MS analysis. A small amount of the product D was dissolved in 20 mM citrate buffer (pH 5.0), then processed with N-acetylhexosaminidase, and thereafter analyzed through HPLC.

As a result, the product D was decomposed into N-acetylglucosamine and β-CD in a molar ratio of 1/1. Accordingly, referring to the data in Example 1, the product D was presumed to be a compound (of the above-mentioned structural formula 5 or 9, where n=6) in which the N-acetylglucosaminyl group is bonded to the secondary hydroxyl group of the β-CD ring by β-bonding therebetween.

Example 3

(1) Condensation

Figure 6:
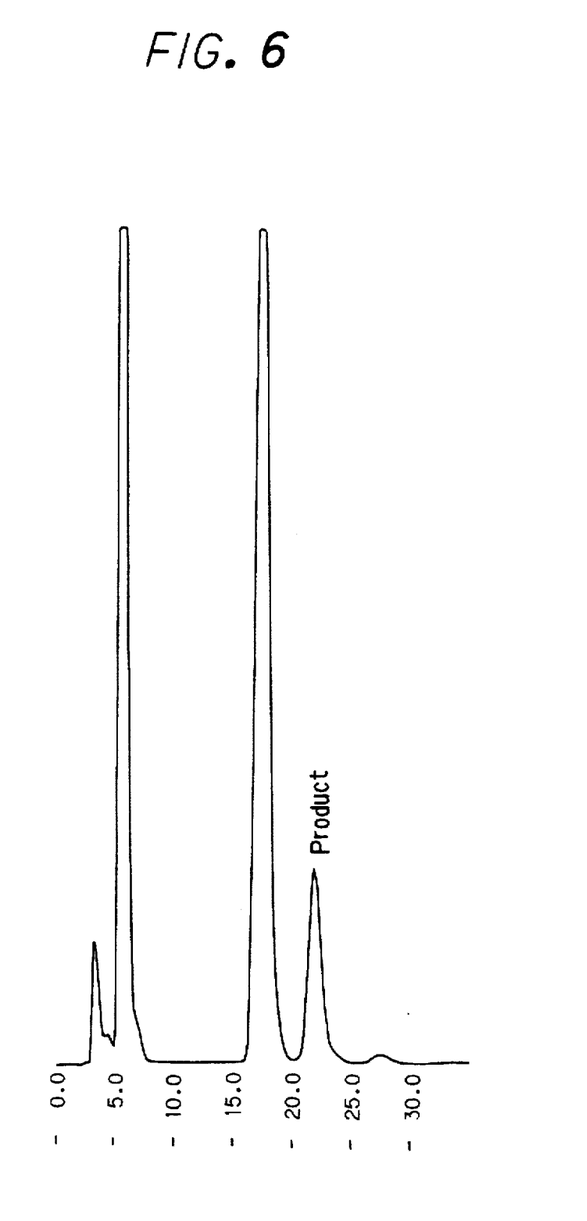
FIG. 6 is a high performance liquid chromatogram of the reaction mixture of Example 3 as passed through an amide type column.

To 5 ml of 20 mM citrate buffer (pH 5.0) containing 1.11 g of N-acetylglucosamine and 1.62 g of γ-CD, added was 50 U of the same N-acetylhexosaminidase as that used in Example 1, and reacted at 45° C. for 72 hours. A part of the reaction mixture was analyzed through high performance liquid chromatography using an amide type column. The data obtained are shown in FIG. 6.

After the reaction, the enzyme was inactivated under heat, and the resulting solution was subjected to high performance liquid chromatography, from which were fractionated 200 mg of a major product E and 6 mg of a minor product F.

(2) Structure Analysis

The major product E as isolated in the above-mentioned step (1) was found to have a molecular weight of 1499 through FAB-MS analysis. Accordingly, referring to the data in Example 1, this product E was confirmed to be a compound (of the above-mentioned structural formula 1, where n=7) in which the N-acetylglucosaminyl group is bonded to the 6-positioned primary hydroxyl group of the γ-CD ring by β-bonding therebetween.

On the other hand, the product F was found to have a molecular weight of 1499 through FAB-MS analysis. A small amount of the product F was dissolved in 20 mM citrate buffer (pH 5.0), then processed with N-acetylhexosaminidase, and thereafter analyzed through HPLC.

As a result, the product F was decomposed into N-acetylglucosamine and γ-CD in a molar ratio of 1/1. Accordingly, referring to the data in Example 1, the product F was presumed to be a compound (of the above-mentioned structural formula 5 or 9, where n=7) in which the N-acetylglucosaminyl group is bonded to the secondary hydroxyl group of the γ-CD ring by β-bonding therebetween.

Example 4

(1) Condensation

Figure 7:
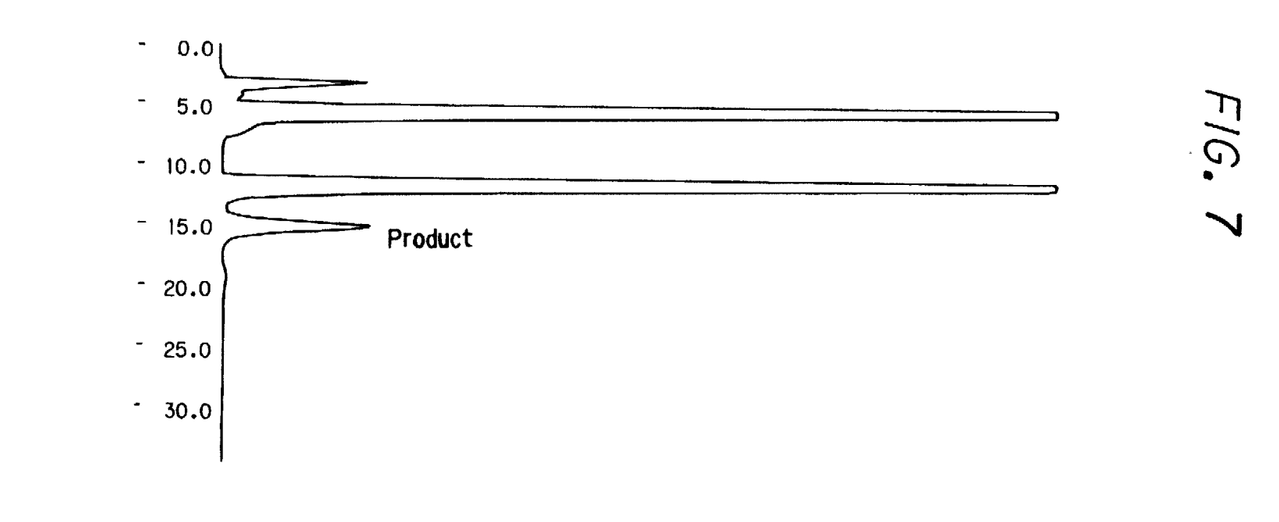
FIG. 7 is a high performance liquid chromatogram of the reaction mixture of Example 4 as passed through an amide type column.
Figure 8:
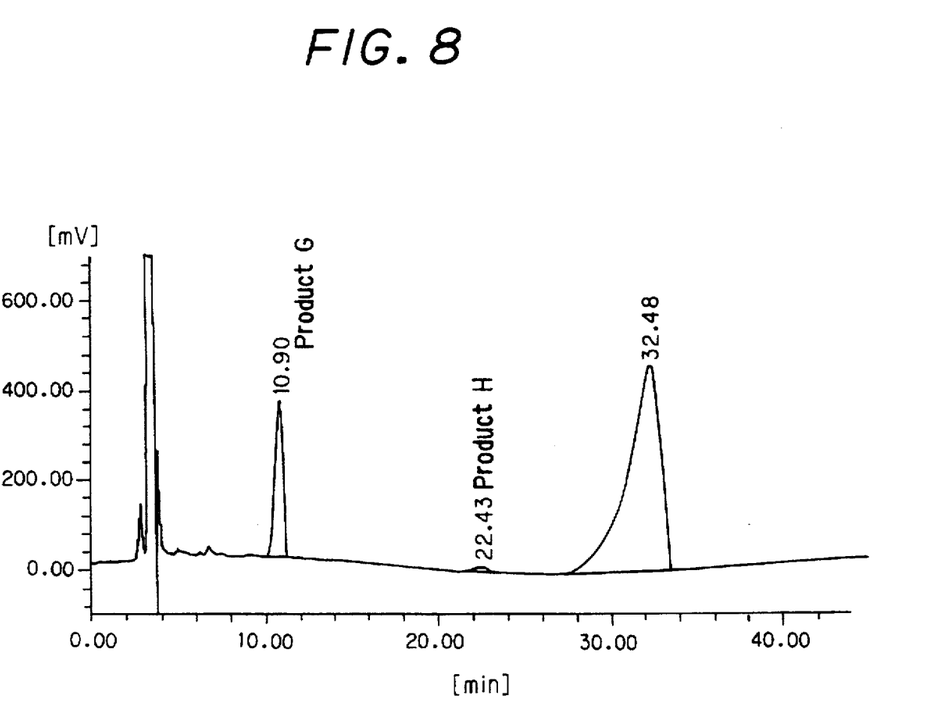
FIG. 8 is a high performance liquid chromatogram of the reaction mixture of Example 4 as passed through a reversed phase type column.

To 5 ml of 20 mM citrate buffer (pH 5.0) containing 1.11 g of N-acetylgalactosamine and 1.22 g of α-CD, added was 50 U of the same N-acetylhexosaminidase as that used in Example 1, and reacted at 45° C. for 72 hours. A part of the reaction mixture was analyzed through high performance liquid chromatography using an amide type column and a reversed phase column. The data obtained are shown in FIG. 7 and FIG. 8.

After the reaction, the enzyme was inactivated under heat, and the resulting solution was subjected to high performance liquid chromatography using a reversed phase column, from which were fractionated 83 mg of a major product G and 5 mg of a minor product H.

(2) Structure Analysis

Figure 9:
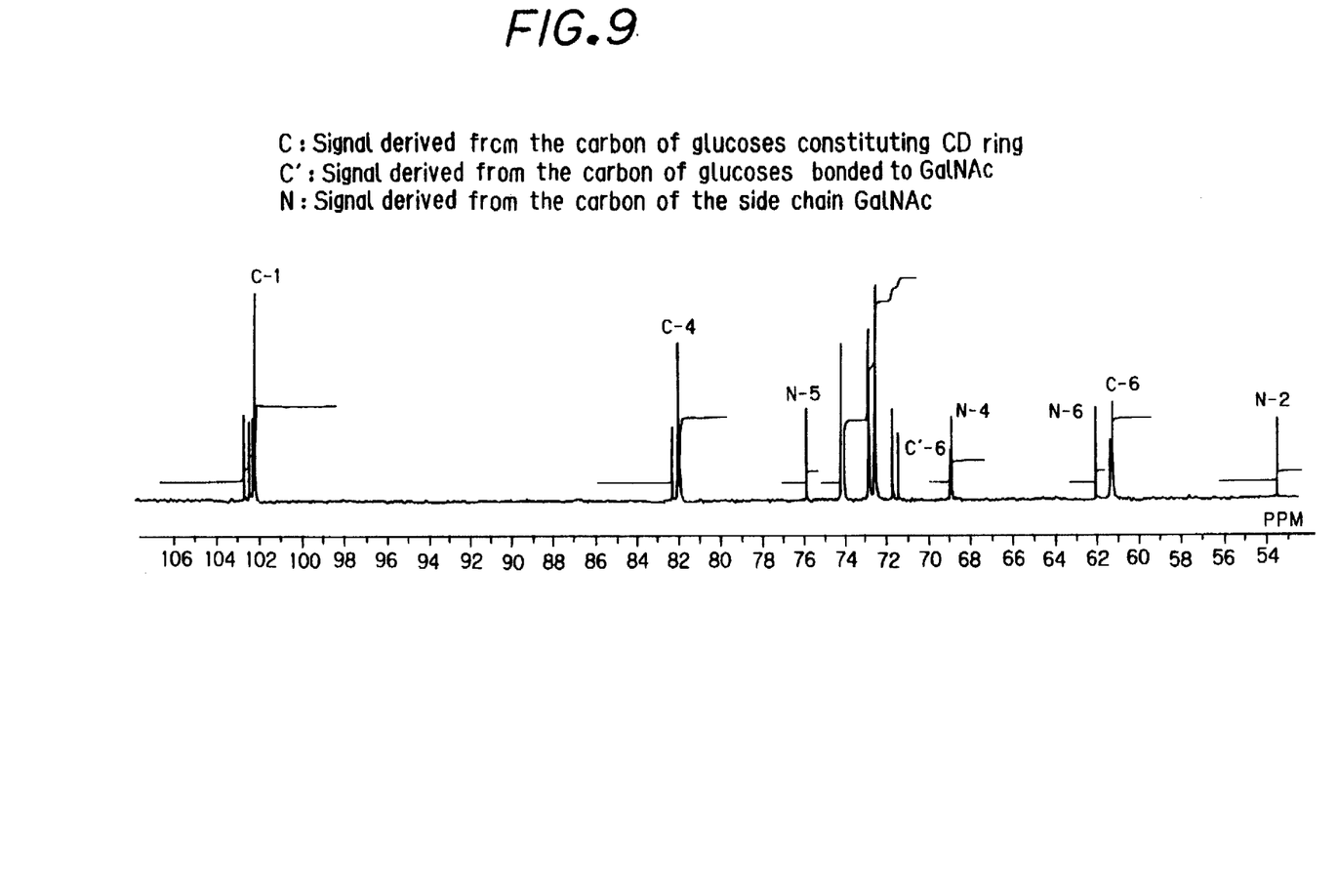
FIG. 9 is a $^{13}$C-NMR spectrum of the reaction product G of Example 4.

The major product G as isolated in the above-mentioned step (1) was found to have a molecular weight of 1175 through FAB-MS analysis. The $^{13}$C-NMR analysis of the product G revealed that this is 6-O-β-D-N-acetylgalactosaminyl-α-CD (of the above-mentioned structural formula 2, where n=5) in which the N-acetylgalactosaminyl group is bonded to the 6-positioned primary hydroxyl group of the α-CD ring by β-bonding therebetween.

On the other hand, the product H was found to have a molecular weight of 1175 through FAB-MS analysis. A small amount of the product H was dissolved in 20 mM citrate buffer (pH 5.0), then processed with N-acetylhexosaminidase, and thereafter analyzed through HPLC. As a result, the product H was decomposed into N-acetylgalactosamine and α-CD in a molar ratio of 1/1. This verifies that the product H is a compound (of the above-mentioned structural formula 6 or 10, where n=5) in which the N-acetylgalactosaminyl group is bonded to the secondary hydroxyl group of the α-CD ring by β-bonding therebetween.

Example 5

25 mg of N-acetylglucosaminyl-α-CD (of the above-mentioned structural formula 1, where n=5) that had been obtained in Example 1 was dissolved in 20% sodium hydroxide solution to have a concentration thereof of 1%, which was thus reacted therein at 80° C. for 3 hours.

After the reaction, concentrated hydrochloric acid was dropwise added to the reaction mixture to neutralize it. Then, the reaction mixture was desalted, using a desalting device (Microacilizer G1, produced by Asahi Chemical Industry Co.), from which was obtained 20 mg of a deacetylated product, or that is, a compound (of the above-mentioned structural formula 3, where n=5) in which the glucosaminyl group is bonded to the 6-positioned hydroxyl group of the α-CD ring by β-bonding therebetween.

Example 6

25 mg of N-acetylgalactosaminyl-α-CD (of the above-mentioned structural formula 2, where n=5) that had been obtained in Example 4 was dissolved in 20% sodium hydroxide solution to have a concentration thereof of 1%, which was thus reacted therein at 80° C. for 3 hours.

After the reaction, concentrated hydrochloric acid was dropwise added to the reaction mixture to neutralize it. Then, the reaction mixture was desalted, using a desalting device (Microacilizer G1, produced by Asahi Chemical Industry Co.), from which was obtained 20 mg of a deacetylated product, or that is, a compound (of the above-mentioned structural formula 4, where n=5) in which the galactosaminyl group is bonded to the 6-positioned hydroxyl group of the α-CD ring by β-bonding therebetween.

As has been described in detail hereinabove with reference to the embodiments thereof, the present invention efficiently produces novel branched CDs having an N-acetylglucosaminyl group or N-acetylgalactosaminyl group as bonded to the hydroxyl group of the CD ring by β-bonding therebetween, while utilizing enzymatic condensation. The deacetylation of these branched CDs efficiently gives novel branched CDs having a glucosaminyl group or galactosaminyl group as bonded to the hydroxyl group of the CD ring by β-bonding therebetween.

These novel branched CDs of the present invention are expected to be widely usable not only in the field of medicines but also in the field of foods and cosmetics.

While the invention has been described in detail and with reference to specific embodiments thereof, it will be apparent to one skilled in the art that various changes and modifications can be made therein without departing from the spirit and scope thereof.

The entire disclosure of Japanese Patent Application No. 199534/1996 filed on Jul. 11, 1996 including specification, claims, drawings and summary are incorporated herein by reference in its entirety.

What is claimed is:

1. A branched cyclodextrin comprising a group selected from the group consisting of an N-acetylglucosaminyl group, a glucosaminyl group, an N-acetylgalactosaminyl group and a galactosaminyl group which is bonded to a hydroxyl group of a cyclodextrin ring by β-bonding, and salts of said branched cyclodextrin.

2. The branched cyclodextrin and salts thereof of claim 1, wherein the cyclodextrin is an unsubstituted α-cyclodextrin, β-cyclodextrin or γ-cyclodextrin, or an α-cyclodextrin, β-cyclodextrin or γ-cyclodextrin which is substituted by a substituent which is bonded by β-1,6 bonding to at least one hydroxyl group of the cyclodextrin ring.

3. The branched cyclodextrin and salts thereof of claim 1, wherein the branched cyclodextrin is selected From the group consisting of 6-O-β-D-N-acetylglucosaminyl-α-CD, 6-O-β-D-N-acetylglucosaminyl-β-CD, 6-O-β-D-N-acetylglucosaminyl-γ-CD, 6-O-β-D-N-acetylgalactosaminyl-α-CD, 6-O-β-D-N-acetylgalactosaminyl-β-CD, 6-O-β-D-N-acetylgalactosaminyl-γ-CD, 6-O-β-D-glucosaminyl-α-CD, 6-O-β-D-glucosaminyl-β-CD, 6-O-β-D-glucosaminyl-γ-CD, 6-O-β-D-galactosaminyl-α-CD, 6-O-β-D-galactosaminyl-β-CD, 6-O-β-D-galactosaminyl-γ-CD, 3-O-β-D-N-acetylglucosaminyl-α-CD, 3-O-β-D-N-acetylglucosaminyl-β-CD, 3-O-β-D-N-acetylglucosaminyl-γ-CD, 3-O-β-D-N-acetylgalactosaminyl-α-CD, 3-O-β-D-N-acetylgalactosaminyl-β-CD, 3-O-β-D-N-acetylgalactosaminyl-γ-CD, 3-O-β-D-glucosaminyl-α-CD, 3-O-β-D-glucosaminyl-β-CD, 3-O-β-D-glucosaminyl-γ-CD, 3-O-β-D-galactosaminyl-α-CD, 3O-β-D-galactosaminyl-β-CD, 3-O-β-D-galactosaminyl-γ-CD, 2-O-β-D-N-acetylglucosaminyl-α-CD, 2-O-β-D-N-acetylglucosaminyl-β-CD, 2-O-β-D-N-acetylglucosaminyl-γ-CD, 2-O-β-D-N-acetylgalactosaminyl-α-CD, 2-O-β-D-N-acetylgalactosaminyl-β-CD, 2-O-β-D-N-acetylgalactosaminyl-γ-CD, 2-O-β-D-glucosaminyl-α-CD, 2-O-β-D-glucosaminyl-β-CD, 2-O-β-D-glucosaminyl-γ-CD, 2-O-β-D-galactosaminyl-α-CD, 2-O-β-D-galactosaminyl-β-CD and 2-O-β-D-galactosaminyl-γ-CD, wherein CD is the cyclodextrin.

4. The branched cyclodextrin and salts thereof of claim 1, wherein the branched cyclodextrin has a structure selected from the group consisting of and 5. A method for producing the branched cyclodextrin of claim 1, which comprises reacting a solution containing a cyclodextrin and a compound selected from the group consisting of an N-acetylglucosamine and an N-acetylgalactosamine, with an N-acetylhexosaminidase, and optionally deacetylating the resulting product.

6. The method of claim 5, wherein the cyclodextrin is unsubstituted or substituted and is selected from the group consisting of at least one of an α-cyclodextrin, β-cyclodextrin and γ-cyclodextrin.

7. The method of claim 6, wherein the cyclodextrin is substituted by a substituent and is selected from the group consisting of a glucosyl-CD, a maltosyl-CD, a mannosyl-CD and a galactosyl-CD, wherein CD is a cyclodextrin, and wherein the substituent is bonded to a hydroxyl group of the cyclodextrin ring by α-1,6 bonding.

8. The method of claim 5, wherein the cyclodextrin is in an aqueous solution with the N-acetylglucosamine or the N-acetylgalactosamine; the cyclodextrin is in a concentration of 1 to 40% (w/w); and the N-acetylglucosamine or the N-acetylgalactosamine is in a concentration of 5 to 50% (w/w).

9. The method of claim 5, wherein a ratio by weight of the N-acetylglucosamine or the N-acetylgalactosamine to the cyclodextrin is 1/10 to 50/1.

10. The method of claim 9, wherein the ratio is 1/1 to 5/1.

11. The method of claim 9, wherein the solution is at a pH of 3 to 10 and the reaction is carried out at a temperature of 20° C. to 70° C.

12. The method of claim 9, wherein the solution is at a pH of 4 to 7 and the reaction is carried out at a temperature of 40° C. to 60° C.

13. The method of claim 12, wherein the reaction is carried out for 5 to 200 hours.

14. The method of claim 12, wherein the reaction is carried out for 10 to 50 hours.

15. The method of claim 14, wherein the deacetylating is carried out with a solution of sodium hydroxide at a concentration of 1 to 50 (w/v), at a temperature of 10 to 100° C., for 0.1 to 120 hours and with a concentration of an N-acetylglucosaminyl-cyclodextrin solution or an N-acetylgalactosaminyl-cyclodextrin solution of 0.1 to 50% (w/v).

16. The method of claim 15, wherein the concentration of the N-acetylglucosaminyl-cyclodextrin solution or the N-acetylgalactoaminyl-cyclodextrin solution is 0.5 to 10% (w/v).

* * * * *